US010206943B2

(12) United States Patent
Giori et al.

(10) Patent No.: US 10,206,943 B2
(45) Date of Patent: Feb. 19, 2019

(54) ANTIMICROBIAL COMPOSITIONS

(75) Inventors: Andrea Giori, Milan (IT); Giacomo Mombelli, Milan (IT); Stefano Togni, Milan (IT)

(73) Assignee: INDENA S.P.A., Milan (IT)

(*) Notice: Subject to any disclaimer, the term of this patent is extended or adjusted under 35 U.S.C. 154(b) by 532 days.

(21) Appl. No.: 13/699,406

(22) PCT Filed: May 23, 2011

(86) PCT No.: PCT/EP2011/058332
§ 371 (c)(1),
(2), (4) Date: Jan. 23, 2013

(87) PCT Pub. No.: WO2011/147767
PCT Pub. Date: Dec. 1, 2011

(65) Prior Publication Data
US 2013/0149257 A1   Jun. 13, 2013

(30) Foreign Application Priority Data
May 24, 2010   (IT) .......................... MI2010A000933

(51) Int. Cl.
| | | |
|---|---|---|
| *A61K 8/73* | (2006.01) | |
| *A61K 31/715* | (2006.01) | |
| *A61K 8/97* | (2017.01) | |
| *A61K 9/00* | (2006.01) | |
| *A61K 36/48* | (2006.01) | |
| *A61K 47/06* | (2006.01) | |
| *A61K 47/14* | (2017.01) | |
| *A61K 47/26* | (2006.01) | |
| *A61Q 5/02* | (2006.01) | |
| *A61Q 11/00* | (2006.01) | |
| *A61Q 17/00* | (2006.01) | |
| *A61Q 19/00* | (2006.01) | |
| *A61K 36/28* | (2006.01) | |
| *A61K 36/758* | (2006.01) | |
| *A61K 36/77* | (2006.01) | |
| *A61K 45/06* | (2006.01) | |

(52) U.S. Cl.
CPC .............. *A61K 31/715* (2013.01); *A61K 8/73* (2013.01); *A61K 8/97* (2013.01); *A61K 9/006* (2013.01); *A61K 9/0014* (2013.01); *A61K 9/0034* (2013.01); *A61K 36/28* (2013.01); *A61K 36/48* (2013.01); *A61K 36/758* (2013.01); *A61K 36/77* (2013.01); *A61K 45/06* (2013.01); *A61K 47/06* (2013.01); *A61K 47/14* (2013.01); *A61K 47/26* (2013.01); *A61Q 5/02* (2013.01); *A61Q 11/00* (2013.01); *A61Q 17/005* (2013.01); *A61Q 19/00* (2013.01)

(58) Field of Classification Search
USPC ....................................................... 424/401
See application file for complete search history.

(56) References Cited

U.S. PATENT DOCUMENTS

| | | | | |
|---|---|---|---|---|
| 6,162,393 A | * | 12/2000 | De Bruiju et al. ............. | 422/28 |
| 7,211,567 B1 | * | 5/2007 | Kotani et al. ................... | 514/25 |
| 2010/0279981 A1 | * | 11/2010 | Del Prete et al. .............. | 514/54 |

FOREIGN PATENT DOCUMENTS

| | | |
|---|---|---|
| FR | 2 851 469 | 8/2004 |
| WO | 2005/063186 A1 | 7/2005 |
| WO | 2006/123234 A1 | 11/2006 |
| WO | 2009/040847 A2 | 4/2009 |
| WO | 2009/044423 A1 | 4/2009 |

OTHER PUBLICATIONS

Monica Gray, Airborne Microbes, Retrieved online [Dec. 13, 2013], Retrieved from URL:>http://serc.carleton.edu/NAGTWorkshops/health/case_studies/microbes_air.html>.*
Helichrysum Oil, Retrieved online [Mar. 22, 2015], Retrieved from URL:<https://web.archive.org/web/20100113171850/http://www.healthy-healing-oils.com/helichrysumoil.html>, web archive Jan. 2010.*
Mouth Ulcers, Retrieved online [Mar. 22, 2015], Retrieved from URL:<https://web.archive.org/web/20060306233421/http://www.homeopathicdoctor.ca/Health_Notes/CONCERN/CANKER_1.HTM>, web archive Mar. 2006.*
Anonymous: "Imli-Tamarind-Tamarindus indica-Flora-Trees-Haryana Online—India," Jun. 11, 2009, pp. 1-3, retrieved from the Internet: http://www.haryana-online.com/Flora/imli.htm, retrieved on Jan. 25, 2011, (XP002618788).
Agrawal, et al., "Effect of Piper Longum Linn, Zingiber Officianalis Linn and Ferula Species on Gastric Ulceration and Secretion in Rats," Indian Journal of Experimental Biology, vol. 38, No. 10, pp. 994-998, Oct. 2000 (XP009001799).
Ahua, et al., "Antileishmanial activities associated with plants used in the Malian traditional medicine," Journal of Ethnopharmacology, vol. 110, No. 1, pp. 99-104, Feb. 2007 (XP005879691).
Burgalassi, et al., "Effect of xyloglucan (tamarind seed polysaccharide) on conjunctival cell adhesion to laminin and on corneal epithelium wound healing," European Journal of Ophthalmology, vol. 10, No. 1, pp. 71-76, Jan. 2000 (XP009143782).
Database WPI, Week 200704, Thomson Scientific, App. No. JP 2007-029585 & JP 2006-325447, Dec. 2006 (XP002618789).
Database GNPD (Online) Mintel, Anonymous: "Desert Bloom Ultrabalm", retrieved from www.gnpd.com, Database Accession No. 1054545, Jan. 2009 (XP002618790).

(Continued)

*Primary Examiner* — Nannette Holloman
(74) *Attorney, Agent, or Firm* — Silvia Salvadori, P.C.; Silvia Salvadori

(57) ABSTRACT

The present invention relates to the use as an antimicrobial of tamarind seed polysaccharide (TSP) and to antimicrobial compositions which contain it as active ingredient. Antimicrobial compositions containing TSP are particularly useful for topical administration in the treatment and/or prevention of microbial infections of the skin and mucosa.

4 Claims, No Drawings

(56) References Cited

OTHER PUBLICATIONS

Database GNPD (Online) Mintel, Anonymous: "Maximum Moisture Day Cream", retrieved from www.gnpd.com, Dabatase Accession No. 911809, May 2008 (XP002618791).
Database GNPD (Online) Mintel, Anonymous: "Acne Spot Tx", retrieved from www.gnpd.com, Database Accession No. 850241, Feb. 2008 (XP002618792).
Database WPI, Week 199646, Thomson Scientific, App. No. JP 1996-461243 & JP 8-231347, Sep. 1996 (XP002618798).
Ghelardi, et al., "A mucoadhesive polymer extracted from tamarind seed improves the intraocular penetration and efficacy of rufloxacin in topical treatment of experimental bacterial keratitis", Antimicrobial Agents and Chemotherapy, vol. 48, No. 9, pp. 3396-3401, Sep. 2004 (XP002618794).
Marchetti, et al., "Inhibition of Herpes Simplex Virus Infection by Negatively Charged and Neutral Carbohydrate Polymers," Journal of Chemotheray, vol. 7, No. 2, pp. 90-96, 1995 (XP002618796).
Mastromarino, et al. "Antiviral activity of natural and semisynthetic polysaccharides on the early steps of rubella virus infection," Journal of Antimicrobial Chemotherapy, vol. 39, No. 3, pp. 339-345, Mar. 1997 (XP002618797).
Petronio, et al., "In vitro Effect of Natural and Semi-Synthetic Carbohydrate Polymers on Chlamydia Trachomatis Infection", Chemotherapy, vol. 43, pp. 211-217, Jan. 1997 (XP000980521).
Pietropaolo, et al., "Effect of natural and semisynthetic polymers on rabies virus infection in CER cells," Research in Virology, vol. 144, pp. 151-158, Jan. 1993 (XP022352664).
Sinibaldi, et al., "Effect of Biological and Synthetic Polymers on BK Virus Infectivity and Hemagglutination", Journal of Chemotherapy, vol. 4, No. 1, pp. 16-22, 1992, (XP009143764).
Schroeder, et al. "Molecules in Focus Human Beta-DEFENSIN-2", International Journal of Biochemistry and Cell Biology, Exeter, GB, vol. 31, pp. 645-651, Jan. 1999 (XP002937538).
Ziya Al-Din Abdullah Ibn Al-Baitar, "Al-Jaam'e-li-Mufradaat-al-Advia-wal-Aghzia," vol. I, 13th Century AD, p. 4-8, 1874 AD.
Mohammad Akmal Khan, "Qaraabaadeen Azam wa Akmal" 20th Century AD, pp. 9-12, 1897 AD.
Ziya Al-Din Abdullah Ibn Al-Baitar, "Al-Jaam'e-li-Mufradaat-al-Advia-wal-Aghzia," vol. I, 13th Century AD, p. 13-19, 1874 AD.
Ziya Al-Din Abdullah Ibn Al-Baitar, Al-Jaam'e-li-Mufradaat-al-Advia-wal-Aghzia vol. I (1 3th Century AD), 05 (p. 4-8), (Ref.pg. no.of publication:141 ), 1874 AD, Matba Amra, Cairo, Egypt.†
Mohammad Akmal Khan Qaraabaadeen Azam wa Akmal (2 0th century AD), 04 (p. 9-12), ( Ref.pg. no.of publication:688 ), 1897 AD, Matba Siddiqi Delhi / Matba Mustafai, Delhi, India.†
Ziya Al-Din Abdullah Ibn Al-Baitar, Al-Jaam'e-li-Mufradaat-al-Advia-wal-Aghzia vol. I, (1 3th century AD), 07 (p. 13-19) ( Ref.pg. no.of publication:110-111 ), 1874 AD, Matba Amra, Cairo, Egypt.†

\* cited by examiner
† cited by third party

ANTIMICROBIAL COMPOSITIONS

This application is a U.S. national stage of PCT/EP2011/058332 filed on May 23, 2011, which claims priority to and the benefit of Italian Application No. MI2010A000933, filed on May 24, 2010, the contents of which are incorporated herein by reference.

TECHNICAL FIELD OF THE INVENTION

The present invention relates to the use of tamarind seed polysaccharide as an antimicrobial and to antimicrobial compositions which contain it as active ingredient.

BACKGROUND OF THE INVENTION

Tamarind seed polysaccharide (TSP) is a natural polysaccharide polymer obtained from the seeds of *Tamarindus indica*, an evergreen plant which can reach a height of 15 meters and produces fruit in the form of pods. It is very common in India, Africa and throughout the Far East, where it is mainly grown as a food. The fruit contains large seeds with a high percentage of polysaccharides, which have the function of accumulating and preserving vital energy-giving substances. Tamarind seeds, which were originally considered as waste products, have subsequently found different applications after grinding to obtain a farinaceous product (known as tamarind gum or tamarind nut powder). The most important of these applications is in the textile industry and the paper industry, where tamarind gum is used as a sizing and gluing agent, and in the food industry where, like other polysaccharides, it is used as a thickener, gelling agent, stabiliser and binder in various products. Raw tamarind gum is a commercially available product containing from 65% to 73% by weight of polysaccharide, from 15% to 23% by weight of protein material, from 3% to 8% by weight of fats and oils, and from 2% to 4% by weight of ash, together with smaller amounts of raw fibre, tannins and other impurities.

More recently, TSP has also been used in the pharmaceutical field as active ingredient in tears substitutes (WO2009/044423), as a carrier for slow-release ophthalmic medicaments for topical administration (WO97/28787) and, more generally, as an excipient due to its mucoadhesive characteristics (WO2006/131262).

SUMMARY OF THE INVENTION

The present invention refers to the use of tamarind seed polysaccharide in prevention and/or treatment of microbial infections.

The invention also relates to an antimicrobial pharmaceutical and/or dermocosmetic composition comprising tamarind seed polysaccharide as active ingredient mixed with one or more acceptable excipients.

Furthermore, the invention concerns a method of preventing or treating a patient having a microbial infection comprising administering a therapeutically effective amount of Tamarind seed polysaccharide.

DETAILED DESCRIPTION OF THE INVENTION

We have now found that tamarind seed polysaccharide (hereinafter called TSP) has antimicrobial properties, especially when administered topically.

Object of the present invention is therefore the use of TSP as an antimicrobial and, in particular, the use of TSP as an antimicrobial for topical administration.

A further object of the present invention is an antimicrobial pharmaceutical and/or dermocosmetic composition comprising TSP mixed with one or more acceptable excipients and, more particularly, an antimicrobial pharmaceutical and/or dermocosmetic composition for topical administration comprising TSP mixed with one or more acceptable excipients.

TSP can be used, as an antimicrobial according to the present invention, alone or in combination with other active ingredients.

A further object of the present invention is therefore the use of TSP as an antimicrobial in combination with one or more active ingredients and, more particularly, the use of TSP as an antimicrobial for topical administration in combination with one or more active ingredients.

Antimicrobial pharmaceutical and/or dermocosmetic compositions and, more particularly, antimicrobial pharmaceutical and/or dermocosmetic compositions for topical administration, comprising TSP in combination with one or more active ingredients mixed with one or more acceptable excipients, also form the object of the present invention.

According to the present invention, "TSP" means a polysaccharide-enriched fraction obtained from tamarind gum commercially available, for example from Dainippon Sumitomo Pharma Ltd. under the Glyloid® trademark or from Indena SpA under the Xilogel® trademark.

The active ingredients which can be used in combination with TSP are, for example, antimicrobial agents, anti-inflammatory agents, wound-healing agents.

The preferred antimicrobial agents are antibiotics such as clindamycin, erythromycin, benzylpenicillin, tetracycline, chloramphenicol, vancomycin and linezolid.

Anti-inflammatory agents include steroidal anti-inflammatory drugs, such as cortisone, and non-steroidal anti-inflammatory drugs, such as acetylsalicylic acid and ibuprofen.

Wound-healing agents may be of natural or synthetic origin.

Particularly preferred is the combination of TSP with other extracts of plant origin, especially extracts of plant origin which possess antimicrobial and/or anti-inflammatory and/or wound-healing properties.

The use of TSP in combination with other extracts of plant origin can have a synergic effect on antimicrobial activity.

Preferred examples of extracts of plant origin which may be used in combination with TSP are extracts of *Helichrysum italicum, Echinacea* spp., *Aesculus hippocastanum* and *Zanthoxylum bungeanum*.

The extracts of *Helichrysum italicum, Echinacea* spp. and *Aesculus hippocastanum* are known individually for their antimicrobial action.

The active ingredients in *Helichrysum italicum* extract are contained in the aerial parts of the plant, which contains non-flavonoid prenylated polyphenols. The extracts of *Helichrysum italicum* are known and can be prepared by conventional methods.

The active ingredients of *Echinacea* spp. extract are contained in the aerial part of the plant, which contains echinacoside. The extracts of *Echinacea* spp. are known and can be prepared by conventional methods.

The active ingredients of *Aesculus hippocastanum* extract are contained in the seed and in the bark of the plant, which contains proanthocyanidin A2 (PA2).

The extracts of *Aesculus hippocastanum* are known and can be prepared by known methods.

The active ingredients in *Zanthoxylum bungeanum* extract are contained in the pericarp, which contains alkamides. The extracts of *Zanthoxylum bungeanum* are known and can be prepared by conventional methods.

For use as an antimicrobial according to the present invention, TSP is formulated in suitable pharmaceutical and/or dermocosmetic compositions, preferably in topical pharmaceutical and/or dermocosmetic compositions. The topical pharmaceutical and/or dermocosmetic compositions according to the invention comprise TSP mixed with one or more suitable excipients and may be, for example, in the form of cream, ointment, gel, gum, toothpaste, mouthwash or shampoo.

TSP may generally be used in quantities of between 0.1% and 5% by weight, preferably between 0.1% and 2% by weight, and even more preferably between 0.2% and 1% by weight.

The other active ingredients optionally present in combination with TSP are used in suitable effective quantities. In the case of other extracts of plant origin used in combination with TSP, their quantity is generally between 0.1% and 5% by weight, preferably between 0.1% and 2% by weight, and even more preferably between 0.2% and 1% by weight.

Examples of suitable excipients that may be used in the compositions according to the invention are solvents, diluents, gliding agents, preservatives, gums, sweeteners, coating agents, binders, disintegrating agents, lubricants, suspending agents, dispersing agents, colorants, flavouring agents, non-stick agents, surfactants, plasticisers, emulsifiers, chelating agents and emollients.

The solvent preferably used is water, but alcohols or other organic solvents may also be used, possibly mixed with water.

The choice of excipients is part of the normal knowledge of one skilled in the art, and will mainly depend on the pharmaceutical and/or dermocosmetic form chosen.

For example, a cream can be prepared by incorporating TSP in a topical carrier consisting of liquid paraffin, dispersed in an aqueous medium by means of lubricants. An ointment can be prepared by mixing TSP with a topical carrier such as mineral oil or wax. A gel can be prepared by mixing TSP with a topical carrier containing a gelling agent.

The pharmaceutical and/or dermocosmetic composition according to the invention may also be a, woven or non-woven, material coated and/or impregnated with a mixture of TSP with a suitable carrier or a matrix in which TSP is dispersed so that it comes into contact with the skin for transdermal administration. Specific examples are sticking plasters, gauze, towelettes, etc.

The choice of type of pharmaceutical and/or dermocosmetic form will depend mainly on the area to be treated and is part of the normal knowledge of one skilled in the art. For example, a gum or mouthwash may be more suitable to treat the oral cavity, whereas a cream, ointment, lotion or towelettes may be suitable for the skin of the face.

The treatment with TSP according to the present invention is effective in stimulating the antimicrobial response, especially when administered topically to the skin and to the mucosa.

According to the invention, the term "microbial infection" refers to harmful colonisation of a host organism by one or more microbial species. The host organism can be human or animal, preferably human. The microbe that causes the infection can be a bacterium, a yeast, a virus or a fungus. TSP is particularly indicated for the treatment and/or prevention of bacterial infections.

The compositions according to the invention are therefore useful to treat any disorder of the skin or mucosa caused by the presence of one or more microbes. Contact between the skin or mucosa and a composition according to the invention reduces the bioburden, namely the number of microbes, in the contact area.

The term "skin" is used according to the present in its conventional meaning, namely an external organ including the epithelial tissue. The term "mucosa" is also used with its usual meaning, which relates to all the mucosal barriers in the body, such as the gastrointestinal, pulmonary, sublingual, buccal, rectal, vaginal, nasal, urethral and ocular barriers.

The compositions according to the invention are preferably applied by topical administration directly to the area of the skin or mucosa which presents, or is assumed to present, a microbial infection or other disorders caused by the presence of microbes. The infection often originates in a part of the skin or mucosa which presents a lesion, such as a wound, laceration or burn. In such case, the composition according to the invention can be applied directly to the lesion and/or the surrounding area.

Numerous disorders of the skin and mucosa caused by microbes are known. For example, one disorder of the skin or mucosa which can be effectively treated or prevented by applying a composition according to the invention is the ulcer, i.e. an open wound on the skin or mucosa which is usually caused initially by an abrasion followed by a microbial infection.

Ulcers at every stage (from 1 to 6 in the Merck Manual's classification system) can be treated with the compositions according to the invention. Ulcers are most frequent in patients with diabetes (diabetic ulcers, especially diabetic foot ulcers).

Ulcerations of the oral mucosa can also be treated with the compositions according to the invention.

In particular, TSP can be used for the topical treatment of mucositis and stomatitis.

The terms mucositis and stomatitis are often used interchangeably, although the two disorders can present some differences.

Mucositis is a toxic inflammatory reaction which affects the gastrointestinal tract and can be caused by exposure to chemotherapy agents or ionising radiation. Mucositis is generally manifested as an erythematous lesion similar to a burn or as a random ulcerative lesion from focal to diffuse.

Stomatitis is an inflammatory reaction that affects the oral mucosa, with or without ulceration, which can be caused or intensified by pharmacological treatments, especially chemotherapy, or by radiotherapy.

The degree of stomatitis can range from mild to severe and the patient with severe stomatitis may be unable to eat or drink or take medicinal products by mouth.

Many women suffer from mouth ulcers at certain stages of the menstrual cycle and at the same time present the same type of ulcers in the genital tract, especially the vulva and vagina. They are sometimes very severe and can cause urine retention and require strong analgesics and sedatives. The most serious is known as Behçet's Syndrome.

According to the invention, the more general term of mucositis will also be used to indicate stomatitis.

Erythematous mucositis may appear as early as three days after exposure to chemotherapy or radiotherapy, but more commonly appears after 5-7 days. The progress to ulcerative mucositis takes place within 7 days of the start of chemotherapy and can sometimes become so severe as to require discontinuance of the pharmacological treatment. Mucositis can involve the mouth and the oropharyngeal tract as well as the gastrointestinal tract from mouth to anus. In the present context, unless otherwise specified, reference is made to mucositis which relates to the more easily accessible regions such as the mouth, pharynx, oesophagus and rectum.

As a high percentage (30-40%) of patients who receive chemotherapy develop mucositis of varying degrees of severity, there is a particular need for an effective, convenient treatment. No effective treatment is currently available, and attempts to solve the problem involve the use of analgesics, antiseptics and oral hygiene measures or attenuation of the symptoms.

Moreover, the problem is not limited to cancer patients, because mucositis frequently also occurs in patients with HIV, especially when associated with Kaposi's sarcoma, in patients suffering from non-Hodgkin's lymphoma, in debilitated elderly patients and in patients receiving treatments with BRMs (Biological Response Modifiers) such as interleukin-2, interferons, lymphocytes activated by lymphokines and the like.

The following examples are provided to further illustrate the present invention.

EXAMPLES

Example 1—Cream for Topical Use

| | |
|---|---|
| TSP (tamarind seed polysaccharide) | 0.200% (w/w) |
| Aesculus hippocastanum extract | 0.200% (w/w) |
| Helichrysum italicum extract | 0.200% (w/w) |
| Water | 75.150% (w/w) |
| Montanov 202 | 5.000% (w/w) |
| Lanol 99 | 10.000% (w/w) |
| Sepilift DPHP | 1.000% (w/w) |
| Monoi Butter | 2.000% (w/w) |
| Sepifeel One | 1.000% (w/w) |
| Aquaxyl | 3.000% (w/w) |
| Panthenol | 1.000% (w/w) |
| Tocopheryl acetate | 0.600% (w/w) |
| Sepicide HB | 0.300% (w/w) |
| Perfume | 0.250% (w/w) |
| Sodium hydroxide (30% sol.) | 0.100% (w/w) |
| Total | 100.000% (w/w) |

Example 2—Oral Paste

| | |
|---|---|
| TSP (tamarind seed polysaccharide) | 0.300% (w/w) |
| Aesculus hippocastanum extract | 0.200% (w/w) |
| Zanthoxylum bungeanum extract | 0.100% (w/w) |
| Sorbitol | 50.000% (w/w) |
| Distilled water | 35.040% (w/w) |
| Hydrated silica | 8.000% (w/w) |
| Carboxymethylcellulose | 5.000% (w/w) |
| Potassium sorbate | 0.300% (w/w) |
| Sodium benzoate | 0.300% (w/w) |
| PEG-40 hydrogenated castor oil | 0.160% (w/w) |
| Sodium saccharine | 0.100% (w/w) |
| Flavouring | 0.500% (w/w) |
| Total | 100.000% (w/w) |

Example 3—Vaginal Cream

| | |
|---|---|
| TSP (tamarind seed polysaccharide) | 0.200% (w/w) |
| Aesculus hippocastanum extract | 0.200% (w/w) |
| Distilled water | 73.300% (w/w) |
| Liquid paraffin | 15.000% (w/w) |
| Cetearyl alcohol - PEG-20 stearate | 9.000% (w/w) |
| Dimethicone | 1.000% (w/w) |
| Phenoxyethanol | 0.500% (w/w) |
| Imidazolidinyl urea | 0.300% (w/w) |
| Propylparaben | 0.150% (w/w) |
| Methylparaben | 0.150% (w/w) |
| Sodium EDTA | 0.100% (w/w) |
| Lactic acid | 0.100% (w/w) |
| Total | 100.000% (w/w) |

Example 4—Beta Defensin Expression in NHEK

Human keratinocytes were cultured in Dulbecco's Modified Eagle Medium with 10% FBS (fetal bovine serum) and 10 ml/L penicillin/streptomycin. NHEK (normal human epidermal keratinocyte) primary human keratinocytes were cultured in KGM (Keratinocyte Growth Medium) in a serum-free environment. Cells were cultured in medium alone (negative reference) or in medium added with LPS (lipopolysaccharides, positive reference) from Escherichia coli (5 mcg/ml).

Different standardized botanical extracts (at 0.2% concentration in the LPS free medium) either alone or in combination with Tamarind Seed Polysaccharide (at 0.2% concentration in the LPS free medium) were diluted in the LPS free medium with cultured keratynocites in Petri dishes. The details are reported in Table 1.

TABLE 1

| Products | Concentration |
|---|---|
| Negative ref. (control) | — |
| Positive ref. (LPS) | 5 mcg/ml |
| Tamarind Seed Polysaccharide (TSP) | 0.2% |
| Helichrysum italicum extract (HIE) | 0.2% |
| HIE + TSP | 0.2% + 0.2% |
| Aesculus hyppocastanum extract (AHE) | 0.2% |
| AHE + TSP | 0.2% + 0.2% |
| Echinacea extract (EE) | 0.2% |
| EE + TSP | 0.2% + 0.2% |
| Zanthoxylum alatum (ZA) | 0.2% |
| ZA + TSP | 0.2% + 0.2% |

The overall expression of DEFB2 (β-defensin 2) was quantified after 18 hours of incubation in NHEK cell supernatants using an enzyme immunoassay kit (ELISA). Results are reported in Table 2.

TABLE 2

| Tested products | DEFB2 Expression (pg/ml) |
|---|---|
| Negative ref. (control) | 0 |
| Positive ref. (LPS) | 12 |
| Tamarind Seed Polysaccharide (TSP) | 40* |
| Helichrysum italicum extract (HIE) | 21 |
| HIE + TSP | 140* |
| Aesculus hyppocastanum extract (AHE) | 23 |
| AHE + TSP | 158* |
| Echinacea extract (EE) | 27 |

TABLE 2-continued

| Tested products | DEFB2 Expression (pg/ml) |
|---|---|
| EE + TSP | 164* |
| Zanthoxylum alatum (ZA) | 32* |
| ZA + TSP | 170* |

*p < 0.001 vs. control

The invention claimed is:

1. Method for topical treatment of mucositis in cancer patients, patients with HIV, patients suffering from non-Hodgkin's lymphoma, diabetes Behçet's Syndrome, elderly patients and in patients receiving treatment with Biological Response Modifiers, said method comprising administering an effective amount of tamarind seed polysaccharide in combination with either an effective amount of an extract of Helicrysum italicum or with an effective amount of an extract of Echinacea ssp, wherein said effective amount comprises 0.2% of the tamarind seed polysaccharide; 0.2% of the extract of Helicrysum italicum and 0.2% of the extract of Echinacea ssp.

2. A pharmaceutical and/or dermocosmetic composition for topical administration containing 0.2% tamarind seed polysaccharide in combination with either 0.2% of an extract of Helichrysum italicum or with 0.2% of an extract of Echinacea ssp., as active ingredients mixed with one or more acceptable excipients.

3. A composition according to claim 2, in the form of cream, ointment, gel, gum, toothpaste, mouthwash or shampoo.

4. A composition according to claim 2, comprising at least a further active ingredient selected from the group consisting of antimicrobial agents, anti-inflammatory agents and wound-healing agents.

* * * * *